US008229740B2

(12) United States Patent
Nordholm et al.

(10) Patent No.: US 8,229,740 B2
(45) Date of Patent: Jul. 24, 2012

(54) APPARATUS AND METHOD FOR PROTECTING HEARING FROM NOISE WHILE ENHANCING A SOUND SIGNAL OF INTEREST

(75) Inventors: Sven Erik Nordholm, Willetton (AU); Kevin Fynn, Mount Lawley (AU)

(73) Assignee: Sensear Pty Ltd., Nedlands (AU)

( * ) Notice: Subject to any disclaimer, the term of this patent is extended or adjusted under 35 U.S.C. 154(b) by 1054 days.

(21) Appl. No.: 11/574,665

(22) PCT Filed: Sep. 7, 2005

(86) PCT No.: PCT/AU2005/001353
§ 371 (c)(1),
(2), (4) Date: Mar. 2, 2007

(87) PCT Pub. No.: WO2006/026812
PCT Pub. Date: Mar. 16, 2006

(65) Prior Publication Data
US 2008/0004872 A1 Jan. 3, 2008

(30) Foreign Application Priority Data
Sep. 7, 2004 (AU) ................................ 2004905082

(51) Int. Cl.
*G10L 21/02* (2006.01)
*G10L 21/00* (2006.01)
*A61F 11/06* (2006.01)
*H04R 1/10* (2006.01)
*H04R 25/00* (2006.01)
*H04B 15/00* (2006.01)
(52) U.S. Cl. ............ 704/226; 704/270; 381/72; 381/74; 381/94.1; 381/313; 381/370; 381/376
(58) Field of Classification Search .................. None
See application file for complete search history.

(56) References Cited

U.S. PATENT DOCUMENTS
3,191,122 A 6/1965 Hussey
(Continued)

FOREIGN PATENT DOCUMENTS
DE 4312155 10/1994
(Continued)

OTHER PUBLICATIONS

Martin Kompis and Norbert Dillier, "Noise reduction for hearing aids: Combining directional microphones with an adaptive beamformer," J. Acoust. Soc. Am. vol. 96, Issue 3, pp. 1910-1913 (1994).*

(Continued)

*Primary Examiner* — Matthew Sked
(74) *Attorney, Agent, or Firm* — Marger Johnson & McCollom PC

(57) ABSTRACT

An apparatus for sound enhancement has at least two microphones (9) that provide a directional microphone array which is arranged to be pointed in the direction of a sound source. The directional microphone array thereby receives sound emitted by the sound source and generates sound signals. A processor (20) processors the sound signals generated by the microphone array to enhance the sound received by the directional microphone array from the sound source relative to other sound received by the directional microphone array. The processor (20) generates a corresponding enhanced signal (ES). Loud speakers (22) reproduce the enhanced signal as audible sound. Furthermore, sound suppression devices (7, 7*a*) are provided to suppress ambient should from reaching the eardrums of the user. This sound suppression acts in conjunction with the directional microphone array and the processor (20) which enhance the SOI to provide a listening environment in which the SOI is enhanced.

19 Claims, 4 Drawing Sheets

U.S. PATENT DOCUMENTS

| | | |
|---|---|---|
| 3,306,991 A | 2/1967 | Wood |
| 4,239,936 A | 12/1980 | Sakoe |
| 4,649,505 A | 3/1987 | Zinser, Jr. et al. |
| 4,654,871 A | 3/1987 | Chaplin et al. |
| 4,897,878 A | 1/1990 | Boll et al. |
| 4,912,767 A | 3/1990 | Chang |
| 5,036,538 A | 7/1991 | Oken et al. |
| 5,125,032 A | 6/1992 | Meister et al. |
| 5,353,376 A | 10/1994 | Oh et al. |
| 5,377,302 A | 12/1994 | Tsiang |
| 5,426,719 A | 6/1995 | Franks et al. |
| 5,550,923 A * | 8/1996 | Hotvet .............. 381/72 |
| 5,574,824 A | 11/1996 | Slyh et al. |
| 5,604,813 A | 2/1997 | Evans et al. |
| 5,646,991 A | 7/1997 | Sih |
| 5,671,158 A | 9/1997 | Fournier et al. |
| 5,727,072 A | 3/1998 | Raman |
| 5,752,226 A | 5/1998 | Chan et al. |
| 5,757,937 A | 5/1998 | Itoh et al. |
| 5,828,997 A | 10/1998 | Durlach et al. |
| 5,966,690 A | 10/1999 | Fujita et al. |
| 6,009,396 A | 12/1999 | Nagata |
| 6,058,194 A | 5/2000 | Gulli et al. |
| 6,104,816 A | 8/2000 | Downs, Jr. et al. |
| 6,128,594 A | 10/2000 | Gulli et al. |
| 6,129,175 A * | 10/2000 | Tutor et al. ............ 181/135 |
| 6,205,425 B1 | 3/2001 | Ho |
| 6,219,645 B1 | 4/2001 | Byers |
| 6,278,786 B1 | 8/2001 | McIntosh |
| 6,363,345 B1 | 3/2002 | Marash et al. |
| 6,424,721 B1 | 7/2002 | Hohn |
| 6,567,524 B1 | 5/2003 | Svean et al. |
| 6,594,370 B1 | 7/2003 | Anderson |
| 6,661,901 B1 | 12/2003 | Svean et al. |
| 6,720,878 B2 | 4/2004 | Jumpertz |
| 6,754,359 B1 | 6/2004 | Svean et al. |
| 6,859,773 B2 | 2/2005 | Breton |
| 6,937,980 B2 | 8/2005 | Krasny et al. |
| 7,031,068 B2 | 4/2006 | Himmele |
| 7,031,483 B2 * | 4/2006 | Boone et al. ............ 381/313 |
| 7,112,965 B2 * | 9/2006 | Scheffler et al. ............ 324/309 |
| 7,519,186 B2 * | 4/2009 | Varma et al. ............ 381/94.7 |
| 7,609,842 B2 * | 10/2009 | Sipkema et al. ............ 381/327 |
| 2002/0069054 A1 | 6/2002 | Arrowood et al. |
| 2002/0120443 A1 | 8/2002 | Epstein et al. |
| 2003/0009329 A1 | 1/2003 | Stahl et al. |
| 2003/0058100 A1 | 3/2003 | Jumpertz |
| 2003/0206624 A1 | 11/2003 | Domer et al. |
| 2004/0097263 A1 | 5/2004 | Katayama et al. |
| 2004/0180691 A1 | 9/2004 | Cascone |
| 2004/0193411 A1 | 9/2004 | Hui et al. |
| 2004/0196984 A1 | 10/2004 | Dame et al. |
| 2004/0261158 A1 | 12/2004 | Depew et al. |
| 2005/0027522 A1 | 2/2005 | Yamamoto et al. |
| 2005/0071158 A1 | 3/2005 | Byford |
| 2005/0117771 A1 | 6/2005 | Vosburgh et al. |
| 2005/0273218 A1 | 12/2005 | Breed et al. |
| 2006/0120537 A1* | 6/2006 | Burnett et al. ............ 381/71.6 |
| 2006/0153394 A1* | 7/2006 | Beasley ............ 381/57 |
| 2007/0100637 A1* | 5/2007 | McCune ............ 704/277 |

FOREIGN PATENT DOCUMENTS

| | | |
|---|---|---|
| DE | 101 17 705 A1 | 10/2001 |
| GB | 2 188 210 A | 9/1987 |
| JP | 4180095 | 6/1992 |
| JP | 5092788 | 4/1993 |
| JP | 8254988 | 10/1996 |
| JP | 11163758 | 6/1999 |
| WO | WO95/30221 | 11/1995 |
| WO | WO 2004/016037 A1 | 2/2004 |
| WO | WO2004016037 | 2/2004 |

OTHER PUBLICATIONS

Saruwatari, H., et al., "Speech Enhancement Using Nonlinear Microphone Array with Noise Adaptive Complementary Beamforming," Acoustics, Speech, and Signal Processing, 2000, ICASSP '00, Proceeding S., 2000 IEEE Int'l. Conf. on Jun. 5-9, 2000, Piscataway, NJ, USA, IEEE, vol. 2, Jun. 5, 2000, pp. 1049-1052.

* cited by examiner

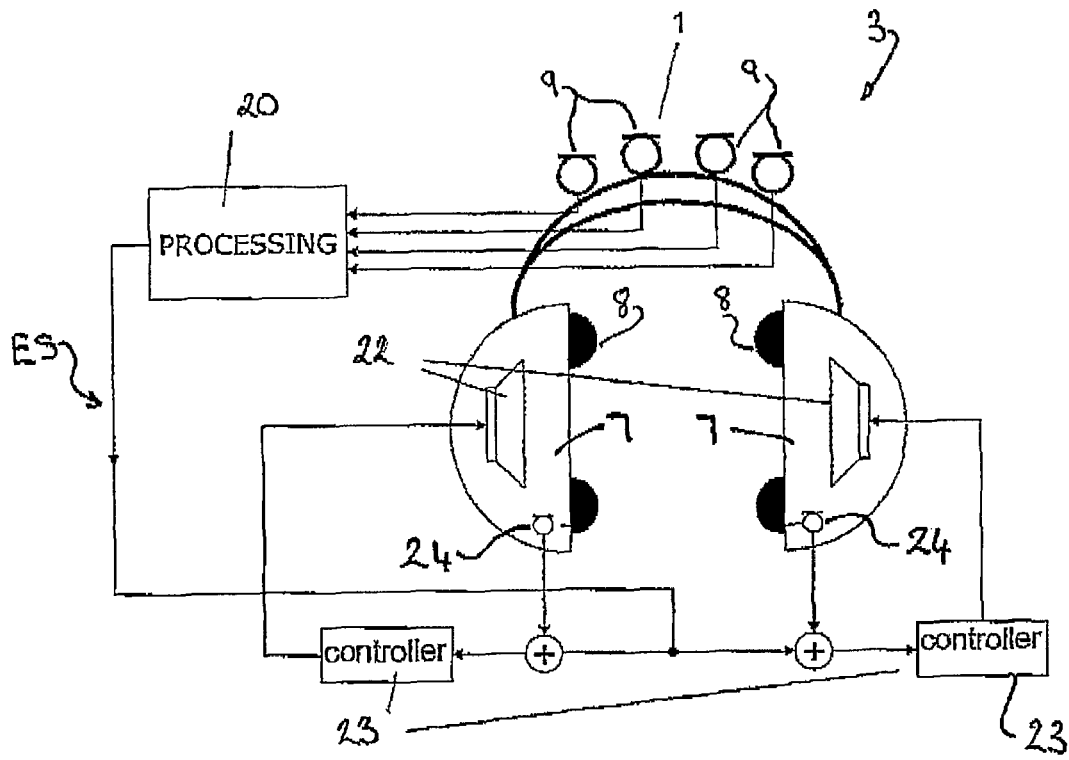
Figure 3
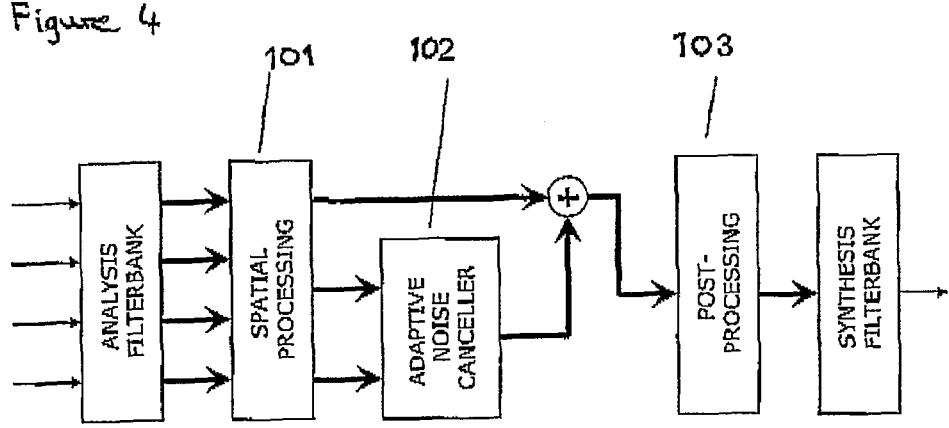

APPARATUS AND METHOD FOR PROTECTING HEARING FROM NOISE WHILE ENHANCING A SOUND SIGNAL OF INTEREST

FIELD OF THE INVENTION

This invention relates particularly to the field of speech communication in adverse acoustic environments such as crowded places, hotels, discotheques, night clubs, industry environments and other noisy environments. However, the present invention is not limited in application to noisy environments where improvements in speech communication is required, but has applicability where a particular sound is to be enhanced in an environment where other, but not required, sounds are present.

BACKGROUND ART

Occupational health is of very serious concern in today's society and people are also becoming more aware of bodily health. To mitigate potential hearing damage in noisy environments, different forms of hearing protection are readily available. However using these hearing protection devices has a negative impact on people's ability to hear and so to communicate.

In addition to the sound source that is desired to be heard being the voice of a person, other environments or situations may require a person to hear a sound, other than a voice of a person, in environments where there is unwanted noise that interferes with this process. Similar considerations as discussed above apply in these situations as well. Thus, whilst in typical situations it is the voice of a person that is desired to be heard over other sounds in the environment, the sound desired to be heard may be other than a human voice.

DISCLOSURE OF THE INVENTION

In accordance with one aspect of the present invention, there is provided an apparatus for sound enhancement comprising:
at least two microphones providing a directional microphone array arranged to be pointed in the direction of a sound source to receive sound emitted by said sound source and generate sound signals,
processing means to process the sound signals generated by said directional microphone array to enhance sound received by said directional microphone array from said sound source relative to other sound received by said directional microphone array and generate a corresponding enhanced signal,
loudspeaker means to reproduce the enhanced signal as audible sound, and
sound suppression means arranged to be located adjacent each ear of the user to suppress ambient sound reaching the ear drums of the user.

Preferably, the sound suppression means provides sound suppression of at least 15 dB.

More preferably, the sound suppression means provides sound suppression in the range of from substantially 15 dB to substantially 50 dB.

Preferably, said processing means provides adaptive processing of the sound signals generated by said directional microphone array dependent upon the levels of the ambient sound in the environment in which the sound source is located.

Preferably, the processing means provides spatial processing, temporal processing and post processing of the sound signals generated by said directional microphone array.

Preferably, the loud speaker means is arranged to be provided adjacent an ear of the user of said apparatus.

The sound suppression means may be provided as a pair of ear muffs.

Alternatively, or additionally, the sound suppression means may be provided as a pair of ear plugs.

In one embodiment, a microphone is provided adjacent each sound suppression means.

Preferably, a controller circuit means is provided which is arranged to receive said enhanced signal prior to said enhanced signal being fed to said loud speaker means and said controller circuit means is arranged to receive sound signals generated by said microphones provided adjacent said sound suppression means prior to being fed to said loud speaker means, wherein the controller circuit means generates cancellation signals to cancel the sound signals generated by said microphones such that reproduction of these sounds at the loud speaker means is attenuated.

The controller circuit means comprises a respective controller circuit for each loud speaker means.

In accordance with another aspect of the present invention, there is provided a method for sound enhancement comprising:
receiving sound signals emitted by a sound source and at least two microphones providing a directional microphone array,
generating sound signals corresponding to the sound received at the directional microphone array,
processing the sound signals generated at said microphone array to enhance sound received by the directional microphone array from said sound source relative to other sound received by said directional microphone array,
generating a corresponding enhanced signal,
reproducing the enhanced signal as audible sound, and
suppressing ambient sound from being heard.

Preferably, suppressing ambient sound provides sound suppression of at least 15 dB.

More preferably, suppressing ambient sound provides sound suppression in the range of from substantially 15 dB to substantially 50 dB.

Preferably, processing the sound signals comprises adaptive processing of the sound signals generated by said directional microphone array dependent upon the levels of the ambient sound in the environment in which the sound source is located.

Preferably, processing the sound signals comprises spatial processing, temporal processing and post processing of the sound signals generated by said directional microphone array.

Preferably, the method further comprises, processing sound signals that are representative of ambient sound that is not suppressed and generating cancellation signals to cancel the ambient sound that is not suppressed such that reproduction of those sounds is attenuated.

Some of the embodiments of the present invention provide a combination of an active and passive headset for suppression of outer noise, along with a multi-microphone system for spatially selective reception of sound desired to be heard and for sound enhancement. The active part (processor and controller circuit) of the headset suppresses the low frequency content of outer sounds and the passive part (earmuffs and earplugs) of the headset the higher frequency content. The multi-microphone system includes a highly directive microphone array that is gain selective in space to the look direction of the sound desired to be heard, e.g. the voice of a speaker, and suppresses reception of sounds from all other directions. The reference to the look direction of the speaker refers to the direction that the user of the apparatus looks to when facing the speaker, i.e. the sound source. It furthermore makes use of a post-filtering technique to further improve the noise suppression and enhance the speech further. The headset can also integrate a wireless communication system to integrate with mobile phones or voice over IP systems.

In one embodiment, the invention can be used as an integrated part of an active/passive earmuff to provide high quality voice input signal while protecting the user from high level noise. The earmuff combines the active noise attenuation in the lower frequency range to assist the speech enhancement technique to operate to its best capability. The use of multi-microphone array technique gives low spatial resolution in the low frequency range and the speech signal is therefore blocked below 200 Hz. Necessary suppression in the low frequency range is of high importance.

In another embodiment, the invention can be integrated into a safety helmet (hardhat) and as such can work under industrial noise environment conditions. This application allows integration of other functions in the helmet, such as RFID, temperature, humidity, movement sensing, and GPS.

In the embodiments of the present invention, the speech enhancement technique utilizes spatial processing from at least two microphone elements that form a directional microphone array. The provision of at least two microphone elements in the microphone array enables directivity, that is spatial separation, of the sound received by the microphone array.

Categories of processing techniques can be blind signal separation (BSS), adaptive beamforming (ABF) or multi-channel spectral subtraction. In order to further enhance the signal it can be combined with post-filtering techniques. It is desirable to maintain the desired speech signal as intact as possible while suppressing the undesired signals. As such, the processing technique includes spatial properties, spectral properties, source distribution and noise characteristics. It is further desirable that the processing provides low delay processing, and that the earmuffs suppress the noise signal over the hearing range to create a relatively noise free environment in the eardrum allowing the wanted speech signal to be injected while maintaining high intelligibility.

BRIEF DESCRIPTION OF THE DRAWINGS

The present invention will now be described, by way of example, with reference to the accompanying drawings, in which:

FIG. 3 shows a schematic diagram of an embodiment of the present invention incorporated into a headset;

FIG. 4 shows an embodiment of the processor functions of the headset shown in FIG. 3.

BEST MODE FOR CARRYING OUT THE INVENTION

Figure 1:
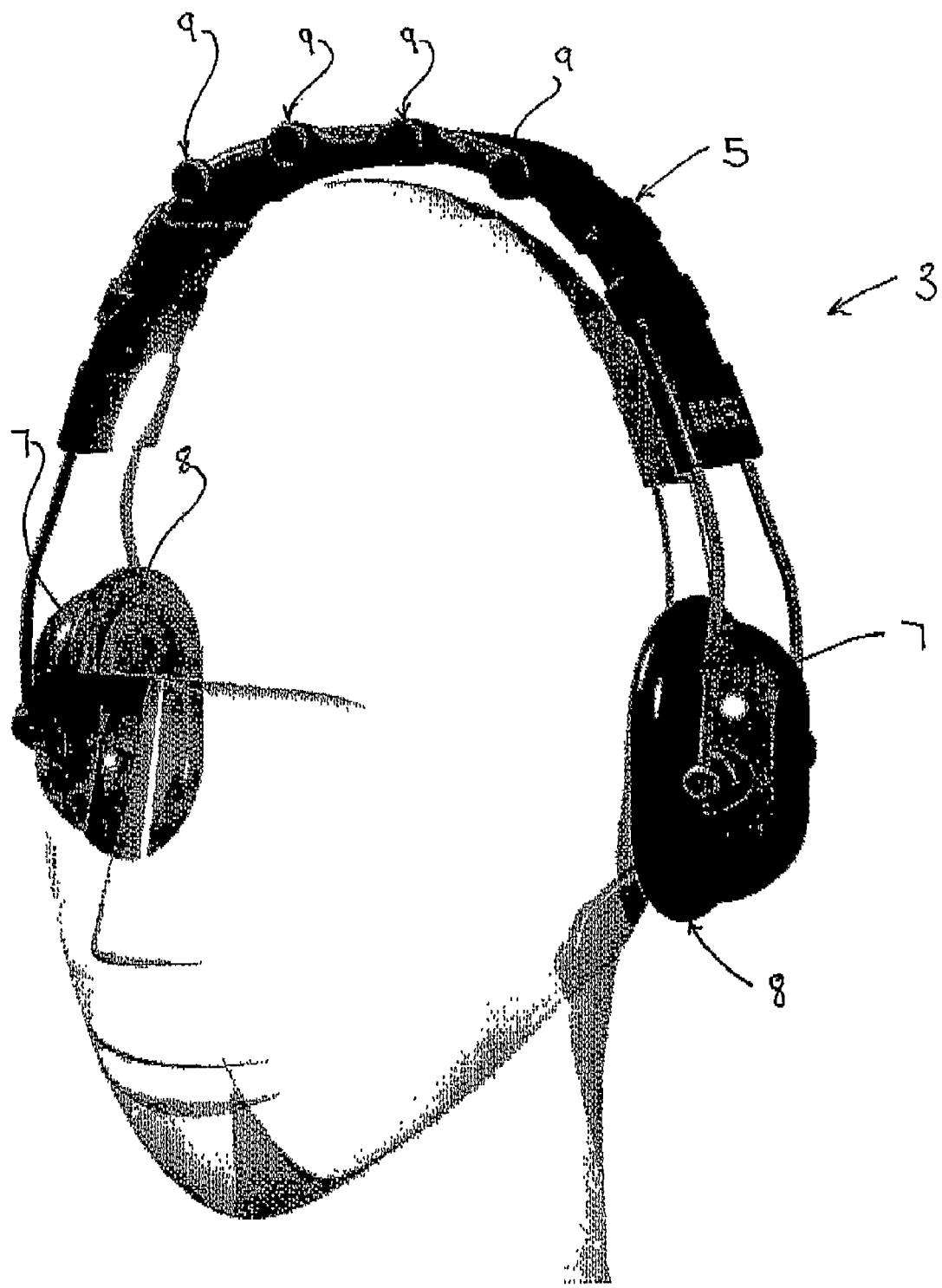
FIG. 1 is an embodiment of the present invention incorporated into a headset to be worn by a wearer.

FIG. 1 illustrates an embodiment of the present invention incorporated into a headset 3. The headset comprises a headband 5 and a pair of ear muffs 7. Loud speakers 22 are provided in the ear muffs 7. Highly directional microphones 9 may be provided on the headband 5 to form a directional microphone array. Such highly directional microphones 9 are more sensitive to reception of sound signals approaching from directly in front of the microphones 9 as compared with sounds approaching from other directions, such as from the rear of the microphones 9, the sides, above or below. Providing at least two such microphones 9 in the array provides the ability to spatially differentiate sounds received for processing as will later be hereinbefore described. Using more that two such microphones 9 in the array improves the ability to spatially differentiate the sounds. In FIG. 1, four such highly directional microphones 9 are shown. The microphones 9 are pointed in the direction in which the wearer of the headset 3 faces the sound source.

The earmuffs 7 are provided with cushions 8. The cushions 8 are flexible and conform to the head of the wearer around the ears of the wearer. The earmuffs 7 suppress ambient sounds, from the environment in which the sound source is located, from reaching the eardrum of the wearer. The suppression of the sounds by the earmuffs is at least 15 dB. A sound suppression of 15 dB would generally be sufficient to suppress unwanted sounds in an environment such as a noisy restaurant. In environments that are noisier, a greater level of suppression is desirable. For example, in an environment such as a nightclub, suppression of approximately 30 dB is desirable. In other environments that are even noisier, greater suppression would be required. Some environments, where the ambient sound is at very high levels, e.g. in the vicinity of aircraft or other industrial environments, suppression of approximately 50 dB is desirable.

Figure 2:
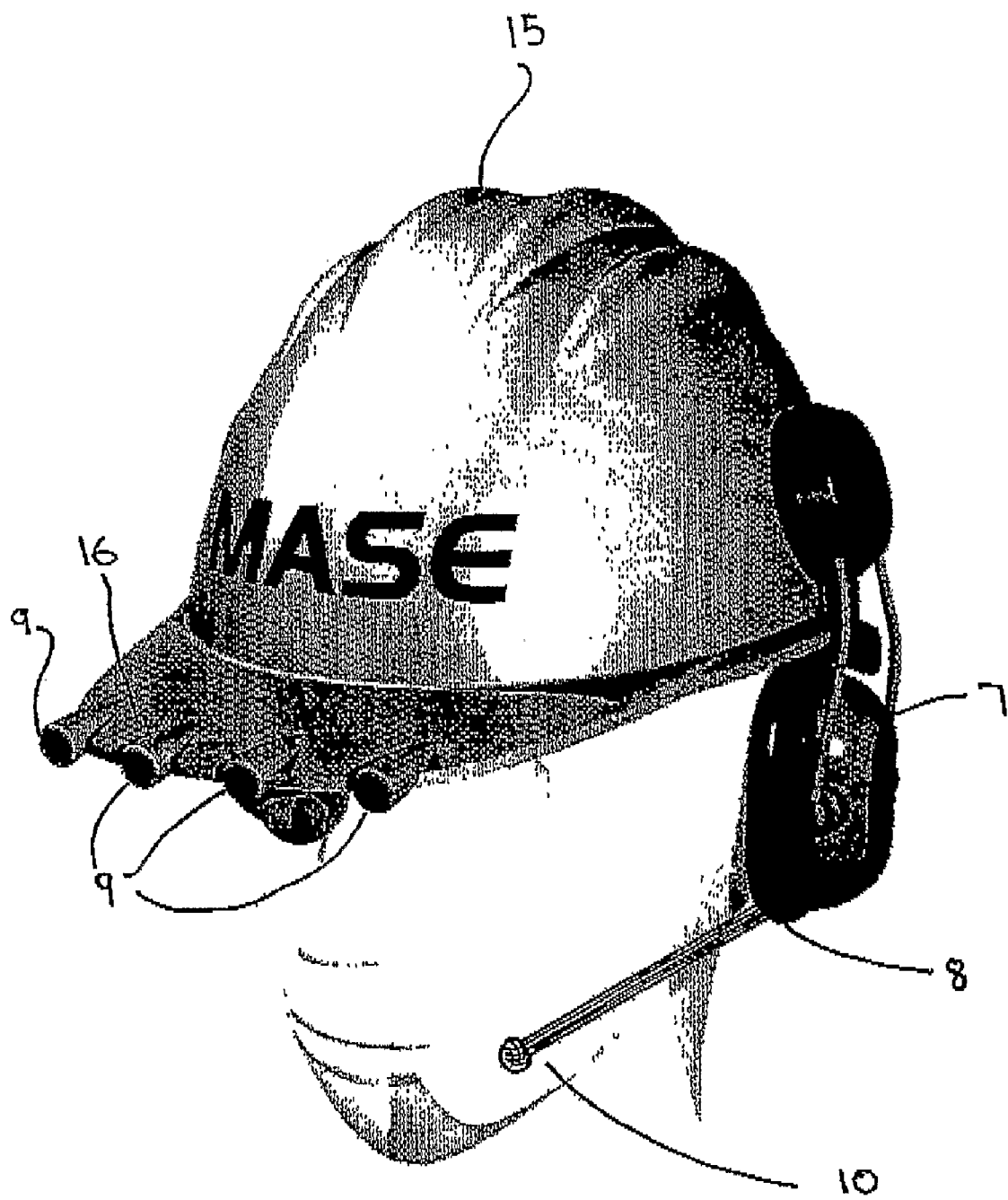
FIG. 2 is a second embodiment of the present invention incorporated into a safety helmet.

FIG. 2 shows an embodiment of the invention incorporated into a safety helmet 15. The highly directional microphones 9 are shown as being positioned on the brim 16 of the helmet 15.

The embodiments shown in FIGS. 1 and 2 are provided for illustration of how the invention can be incorporated into a headset and a safety helmet. Further refinements can be made so that the microphones 9 can be embedded into the structure of the headset 3 and the safety helmet 15 in an acoustically appropriate manner. This would reduce vibrations and self-generated noise caused by the wearer which would enhance the operation of the invention. Additionally, the microphones 9 may be embedded in the headset 3 and the safety helmet 15 to aid the microphones 9 in picking up the sound so that the sound is picked up predominantly from the direction in which the wearer faces. i.e. the "look-direction", which will generally be the direction of the sound source.

Figure 5:
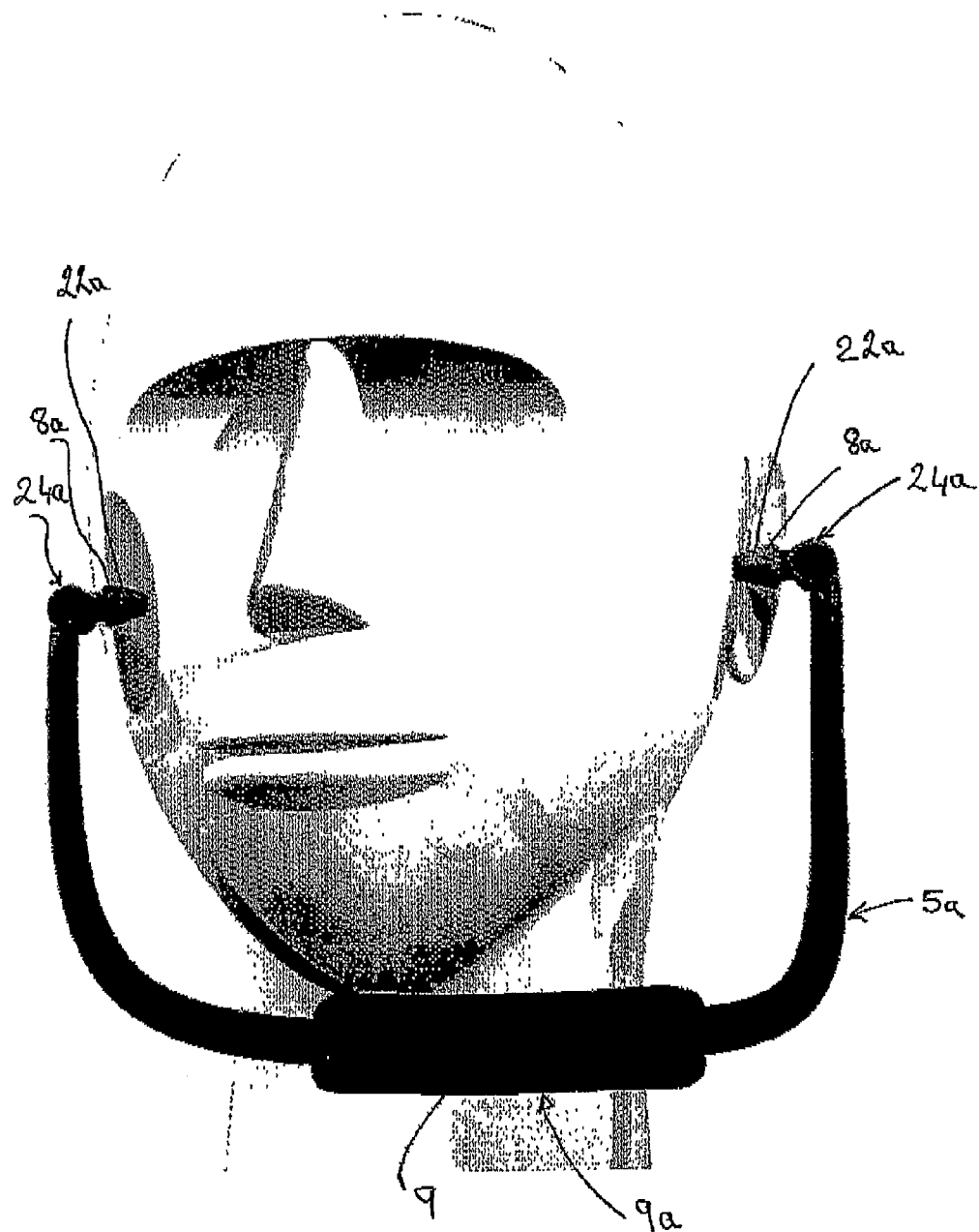
FIG. 5 shows a third embodiment of the present invention incorporated into a headband ear plug set to be worn by a wearer under the chin of the wearer.

The embodiments shown in FIG. 5 illustrates the manner in which the invention can be incorporated into a headband earplug set. The microphones 9 form the directional microphone array 9a. The microphone array 9a is supported by the headband 6a. Earplugs 8a are provided at the ends of the headband 5a. The earplugs 8a may be in form of soft earpieces with inbuilt loud speakers 22a.

A combination of earplugs 8 and earmuffs 7 may also be used. The use of both earplugs 8a and earmuffs 7 provides greater suppression of sounds. The suppression may be approximately 60 dB.

FIG. 2 also illustrates another microphone 10. The microphone 10 is part of a wireless communication system that can be integrated into the safety helmet 15. An antenna that forms part of this communication system may be incorporated into the safety helmet 15. This communication system enables the wearer of the headset 3 or safety helmet 15 to communicate with a remote party. However, it is not, in itself, required for the operation of the present invention.

Additionally, whilst the headset 3, safety helmet 15 and headband earplug set show the microphones 9 incorporated therewith, it is possible that the microphones 9 may be located separate from the headset 3, safety helmet 15 or headband earplug set that is worn by the wearer. The microphones 9 would nevertheless, be directed so as to point in the direction of the sound source whose sound is to be enhanced. As already described herein, the sound source will typically be a person speaking and the sound to be enhanced is the speech of that person so that it is more audible to the person wearing the headset or safety helmet 15.

Referring to FIG. 3 it can be seen that the headset 3 contains four or more microphones 9 which have different functionality due to their spatial position. The microphones 9 are directional microphones pointing forward in the look direction of the wearer of the headset 3. Each microphone 9 in the array receives the sound signal of interest, i.e. sound from the sound source, together with the unwanted (noise) signals. A processor, or speech enhancer, 20 combines spatial information, non-stationary information, temporal information, (noise) envelope distribution information and spectral information to enhance the signal of interest (SOI). The processor 20 incorporates a measurement apparatus that tracks background noise statistics and discriminates between the background noise and the SOI based on their different statistical properties and spatial differentiation. The spatial information obtained from the multiple microphones 9 is beneficial for this purpose in combination with spectral analysis performed by a sub-band filter bank of the processor 20. This allows analysis of the signal and improves spatial processing performed by the processor 20. Additionally, the arrangement allows directional information and also ambient environment information to be included in the signals since two loud speakers 22 are provided. The enhanced signal ES is then fed into both loudspeakers 22.

A microphone 24/24a is mounted close to each loudspeaker 22. Their task is to pick-up the noise, i.e. ambient sound that penetrates the ear muffs 7 or ear plugs 7a, and feed it back to the loudspeakers 22 through respective controller circuits 23. As such, it creates a virtual silence in the microphone point. The enhanced signal ES is also fed to the controller circuits 23. The controller circuits 23 act to cancel the noise in the signals fed to them. The controller circuits 23 generate a signal, referred to as a cancellation signal, corresponding to the ambient sound picked up by the microphones 24/24a. This cancellation signal is fed to the loud speakers 22 and thereby cancels the ambient sound that penetrates the earmuffs 7 or the earplugs 7a. Since the output from the speech enhancer 20 is added into the feedback, i.e. to the controller circuits 23, it is not suppressed by the active headset if the gain of the feedback loop is large.

In other embodiments, the microphones 24/24a may be omitted. This may be done in situations where the unwanted noise penetrating the ear muff 7 or ear plugs 7a is not of a level that requires cancellation. In such case, the enhanced signal ES generated by the processor 20 may be fed direct to the loud speakers 22.

FIG. 4 shows the sound enhancement process of the processor 20. Typically, the sound to be enhanced is a human voice and so the process is also referred to herein as speech enhancement. The speech enhancement processing is divided into three main parts spatial being: processing 1011 temporal processing 102 and post-processing 103. The spatial processing 101 makes use of a spatial differentiation technique in such a manner that if the SOI is spatially located in a position different from that of the noise, it can be separated by a spatial filter. This spatial technique separates the information in the microphones in a number of signals representing different spatial locations. Since it can not be performed perfectly there is still remaining noise to be suppressed in the output of the spatial filter for the SOI. The temporal processing 102 is thus used to further boost the noise suppression. To avoid SOI cancellation it needs to be a controlled process allowing a noise canceller to adapt only when SOI is not active. The temporal processing 102 also incorporates adaptive processing which provides processing that is dependant upon the change in noise levels in the background. To further enhance the signal a post-processing 103 is performed. The post processing 103 uses one channel enhancement techniques such as spectral subtraction. As such, the processing is done in the frequency domain to get a computationally efficient solution.

Throughout the specification, unless the context requires otherwise, the word "comprise" or variations such as "comprises" or "comprising", will be understood to imply the inclusion of a stated integer or group of integers but not the exclusion of any other integer or group of integers.

Modifications and variations such as would be apparent to a skilled addressee are deemed to be within the scope of the present invention.

The claims defining the invention are as follows:

1. A hearing protector for providing enhancement of a sound signal of interest and protection from at least one other sound for a wearer of the hearing protector in an environment that includes high level noise in addition to the sound signal of interest comprising:
    at least two fixed microphones adapted to work together to provide a directional microphone array arranged to be pointed in the wearer's look direction for receiving the sound signal of interest and generating sound signals corresponding to sounds detected at the array,
    a processor to process the sound signals generated by said directional microphone array to enhance the sound signal of interest relative to a signal generated by the high level noise and generate a corresponding enhanced signal,
    at least one speaker operatively connected to the processor for presenting sound based on the enhanced signal to the wearer, and
    at least one passive sound suppressor arranged to be located adjacent each ear of a wearer to suppress the high level noise reaching the ear drums of the wearer, said suppressor able to provide passive sound suppression of at least 15 dB.

2. A hearing protector according to claim 1, wherein the passive sound suppressor provides passive sound suppression in the range of from substantially 15 dB to substantially 50 dB.

3. A hearing protector according to claim 1, wherein said processor provides adaptive processing of the sound signals generated by said directional microphone array dependent upon the levels of ambient sound in the environment in which the sound signal of interest is located.

4. A hearing protector according to claim 1, wherein said processor provides spatial processing, temporal processing and post processing of the sound signals generated by said directional microphone array.

5. A hearing protector according to claim 1, wherein said speaker is arranged to be provided adjacent at least one ear of the wearer.

6. A hearing protector according to claim 1, wherein said hearing protector comprises an ear muff arrangement and wherein said sound suppressor comprises ear muffs.

7. A hearing protector according to claim 1, wherein said sound suppressor comprises ear plugs.

8. A hearing protector according to claim 1, wherein at least one microphone is provided adjacent each sound suppressor.

9. A hearing protector according to claim 8, wherein a controller circuit is provided which is arranged to receive said enhanced signal prior to said enhanced signal being fed to said at least one speaker and said controller circuit is arranged to receive sound signals generated by each said microphone provided adjacent each said sound suppressor prior to being fed to said at least one speaker, and wherein said controller circuit generates cancellation signals to cancel the sound signals generated by each said microphone such that reproduction of these sounds by said at least one speaker is attenuated.

10. An apparatus according to claim 9, wherein said controller circuit comprises a respective controller circuit for each said speaker.

11. A hearing protector according to claim 1, wherein said sound suppressor comprises ear muffs and ear plugs.

12. A method for providing enhancement of a sound signal of interest and protection from at least one other sound for a person in an environment that includes high level noise in addition to the sound signal of interest, the method comprising:
providing at least two fixed microphones working together to provide a directional microphone array arranged to be pointed in the persons look direction for receiving the sound signal of interest,
receiving the sound signal of interest at the microphone array,
generating sound signals corresponding to sound received at said array,
processing the sound signals generated at said array to enhance the sound signal of interest relative to a signal generated by the high level noise,
generating a corresponding enhanced signal,
reproducing the enhanced signal and presenting it to the person, and
passively suppressing the high level noise at the person's ears by at least 15 dB.

13. A method according to claim 12, wherein passively suppressing the high level noise comprises providing sound suppression in the range of from substantially 15 dB to substantially 50 dB.

14. A method according to claim 12, wherein processing the sound signals comprises performing adaptive processing of the sound signals generated by said directional microphone array dependent upon the levels of the ambient sound in the environment in which the sound signal of interest is located.

15. A method according to claim 12, wherein processing the sound signals comprises performing spatial processing, temporal processing and post processing of the sound signals generated by said directional microphone array.

16. A method according to claim 12, further comprising:
processing sound signals that are representative of ambient sound that are not suppressed, and
generating cancellation signals to cancel the ambient sound that is not suppressed such that reproduction of those sounds is attenuated.

17. A method according to claim 12, wherein passively suppressing the high level noise comprises providing ear plugs for the wearer's ears.

18. A method according to claim 12, wherein passively suppressing the high level noise comprises providing ear muffs for the wearer's ears.

19. A method according to claim 12, wherein passively suppressing the high level noise comprises providing ear muffs and ear plugs for the wearer's ears.

* * * * *